US009410197B2

(12) United States Patent
Bergmann et al.

(10) Patent No.: US 9,410,197 B2
(45) Date of Patent: Aug. 9, 2016

(54) COMPOUND FOR SEQUENCING BY SYNTHESIS

(71) Applicant: Roche Diagnostics Operations, Inc., Indianapolis, IN (US)

(72) Inventors: Frank Bergmann, Iffeldorf (DE); Dieter Heindl, Paehl (DE); Jessica Steger-Domandl, Munich (DE)

(73) Assignee: ROCHE MOLECULAR SYSTEMS INC., Pleasanton, CA (US)

( * ) Notice: Subject to any disclaimer, the term of this patent is extended or adjusted under 35 U.S.C. 154(b) by 122 days.

(21) Appl. No.: 14/542,980

(22) Filed: Nov. 17, 2014

(65) Prior Publication Data

US 2015/0140561 A1 May 21, 2015

(30) Foreign Application Priority Data

Nov. 20, 2013 (EP) .................................... 13193588

(51) Int. Cl.
| | |
|---|---|
| C12Q 1/68 | (2006.01) |
| C12P 19/34 | (2006.01) |
| C07H 19/10 | (2006.01) |
| C07H 19/20 | (2006.01) |
| C07H 19/00 | (2006.01) |

(52) U.S. Cl.
CPC .............. *C12Q 1/6869* (2013.01); *C07H 19/10* (2013.01); *C07H 19/20* (2013.01)

(58) Field of Classification Search
CPC ........................ C12Q 1/6869; C12Q 2525/186
USPC ............................ 536/4.1, 23.1; 435/6.1, 91.1
See application file for complete search history.

(56) References Cited

U.S. PATENT DOCUMENTS

| | | | |
|---|---|---|---|
| 5,990,300 | A | 11/1999 | Hiatt et al. |
| 7,057,026 | B2 * | 6/2006 | Barnes et al. ............... 536/23.1 |
| 2007/0117104 | A1 | 5/2007 | Buzby |
| 2008/0138804 | A1 | 6/2008 | Buzby |

FOREIGN PATENT DOCUMENTS

| | | |
|---|---|---|
| DE | 2160104 A1 | 12/1971 |
| WO | 2006/073451 A3 | 7/2006 |

OTHER PUBLICATIONS

Search Report issued Jan. 9, 2014, in European Application No. 13193588.4, 10 pages.
Canard, Bruno and Sarfati, Robert S. "DNA polymerase fluorescent substrates with reversible 3'-tags," Gene, 1994, pp. 1-6, vol. 148.
Duschinsky, R. and Eppenberger, Ursula, "Nitric Acid Esters of Pyrimidine Nucleosides," Tetrahedron Letters, 1967, pp. 5103-1508, No. 50.
Naimi, Ebrahim et al., "Synthesis of 3'- and 5'-Nitrooxy Pyrimidine Nucleoside Nitrate Esters: 'Nitric Oxide Donor' Agents for Evaluation of Anticancer and Antiviral Agents," Journal of Medicinal Chemistry, 2003, pp. 995-1004, vol. 46.

(Continued)

*Primary Examiner* — Jezia Riley
(74) *Attorney, Agent, or Firm* — Olga Kay

(57) ABSTRACT

The present invention provides deoxynucleoside tri- or tetra-phosphate comprising a 3' nitrate and a detectable label covalently bound to the oxygen atom of an oxymethyl or oxyallyl or oxypropargyl substitution of a nucleobase. Such compounds provide new possibilities for future Sequencing by Synthesis technologies.

3 Claims, 3 Drawing Sheets

Synthesis of MR121-labelled 3'-O-nitro-2'-deoxy-β-D-uridine 5'-triphosphate (13)

(56) References Cited

OTHER PUBLICATIONS

Ramanathan, Arvind et al., "High-density polymerase-mediated incorporation of fluorochrome-labeled nucleotides," Analytical Biochemistry, 2005, pp. 1-11, vol. 337.

Wu, Jian et al., "3'-0-modified nucleotides as reversible terminators for pyrosequencing," Proceedings of the National Academy of Sciences, Oct. 2007, pp. 16462-16467, vol. 104, No. 42.

* cited by examiner

Fig. 1: Synthesis of 3'-*O*-nitro-*β*-D-thymidine 5'-triphosphate (3)
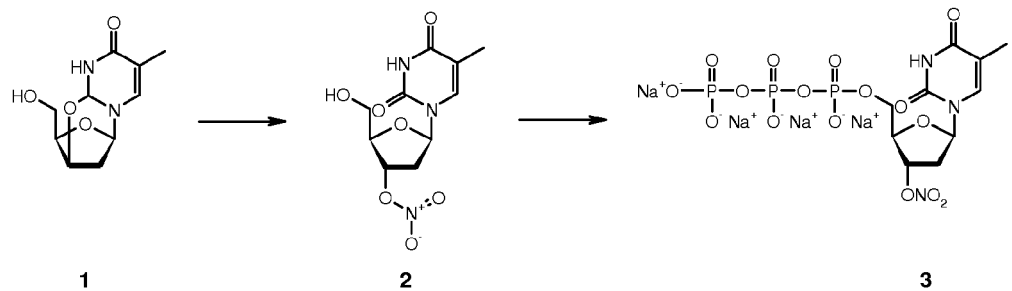
Fig. 2: Synthesis of MR121-PEG$_4$-NHS (6)
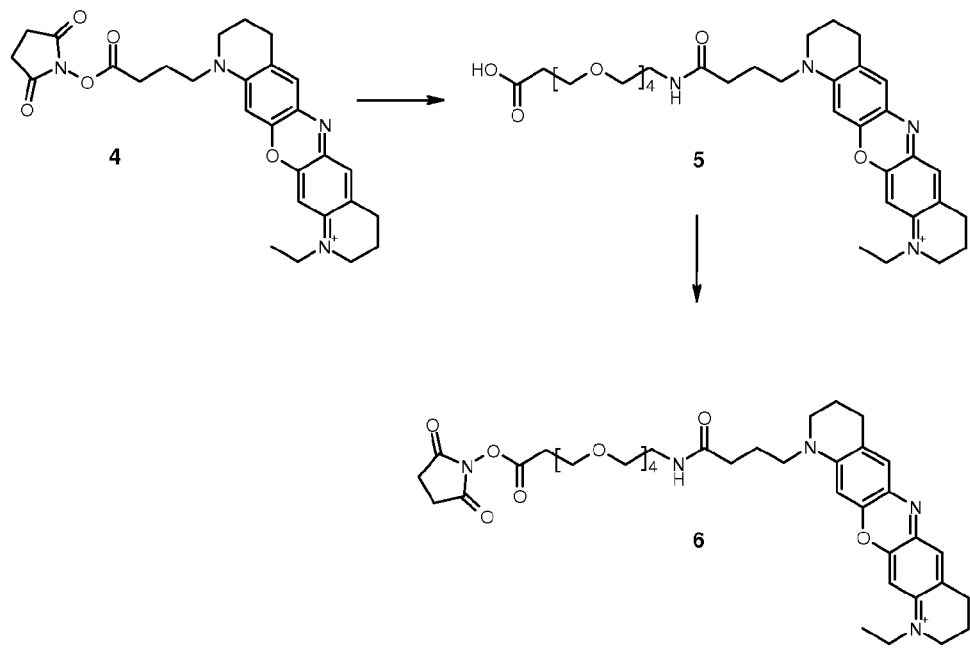

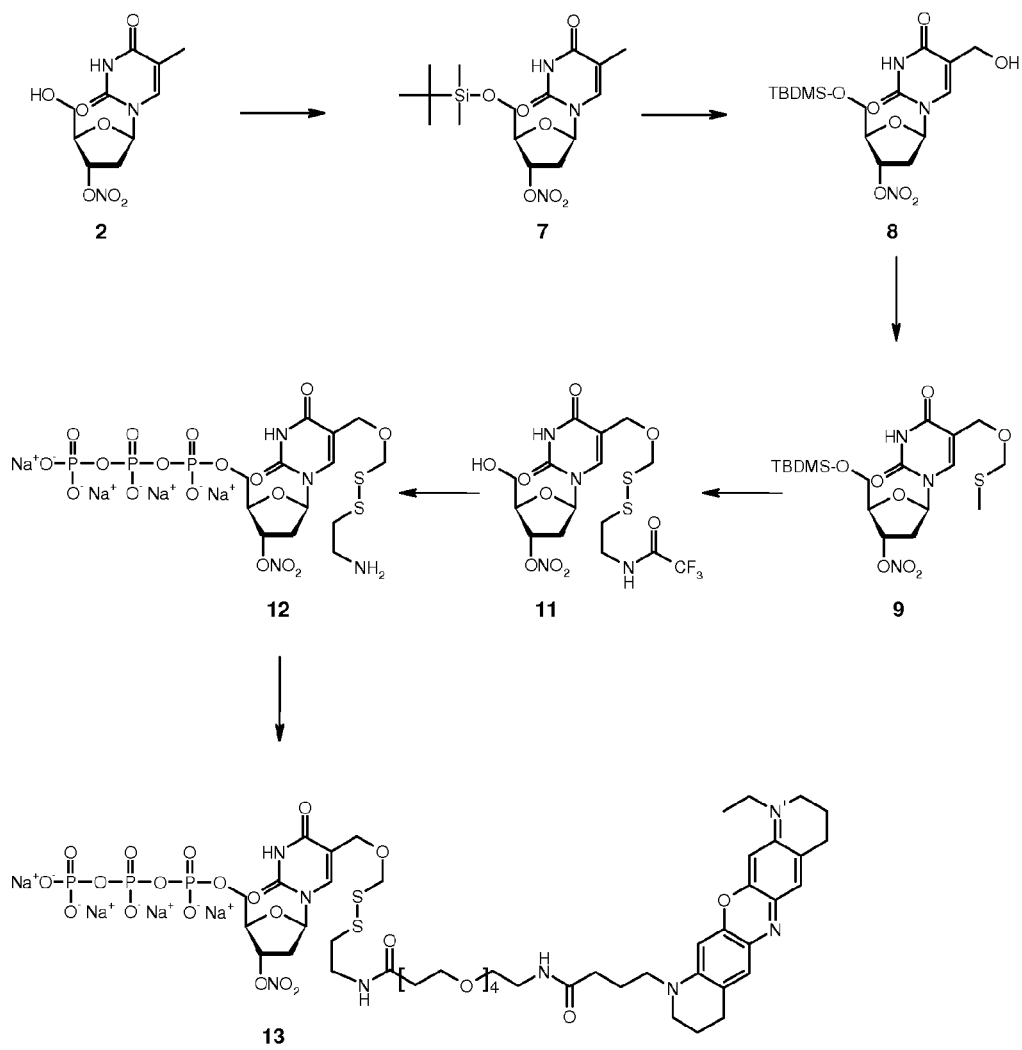
Fig. 3: Synthesis of MR121-labelled 3'-*O*-nitro-2'-deoxy-*β*-D-uridine 5'-triphosphate (13)

Fig. 4: Primer extension experiments
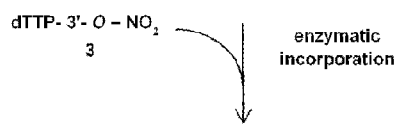
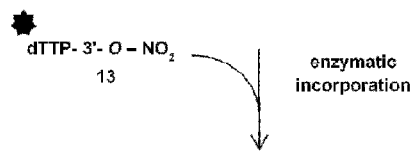
Fig. 5: Cleavage of the 3'-*O*-nitro group
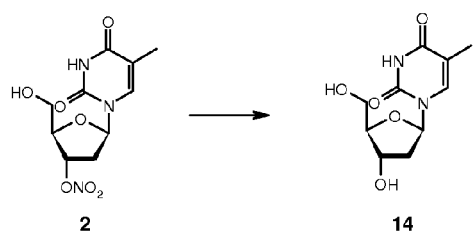

SEQUENCE LISTING

<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: DNA Primer

<400> SEQUENCE: 1
tttcctcctg caccgt                                                       16

<210> SEQ ID NO 2

```
<211> LENGTH: 26
<212> TYPE: DNA
<213> ORGANISM: Artificial Sequence
<220> FEATURE:
<223> OTHER INFORMATION: Template

<400> SEQUENCE: 2
tttggaaagg aggacgtggc aaaaaa                                          26

<210> SEQ ID NO 3
<211> LENGTH: 17
<212> TYPE: DNA
<213> ORGANISM: Artificial Sequence
<220> FEATURE:
<223> OTHER INFORMATION: Primer modified
<220> FEATURE:
<221> NAME/KEY: 3'- nitrate blocking group
<222> LOCATION: (17)..(17)
<223> OTHER INFORMATION: -T-3'-O-NO2

<400> SEQUENCE: 3
tttcctcctg caccgtt                                                   17
```

COMPOUND FOR SEQUENCING BY SYNTHESIS

FIELD OF THE INVENTION

The present invention relates to new compounds for nucleic acid sequencing. The novel compounds are deoxynucleoside triphosphates with a fluorescent label linked to the nucleobase and a removable 3'-nitrate blocking entity. The present invention also provides a method to stabilize such 3' blocking entities.

BACKGROUND OF THE INVENTION

DNA sequencing is one of the most important analytical methods in modern biotechnology. Detailed reviews on current sequencing technologies are provided in M. L. Metzker, Nature Reviews 2010, 11, 31, and C. W. Fuller et al., Nature Biotechnology 2009, 27, 1013.

A well-known sequencing method is the Sequencing-by-synthesis (SBS) method first described by R. Tsien (WO 91/06678). According to this method, the nucleoside triphosphates are reversibly blocked by a 3'-protecting group, in particular esters and ethers. Examples for esters are alkanoic esters like acetyl, phosphates and carbonates. The nucleoside triphosphate usually comprises a label at the base.

A method of enzymatically synthesizing a polynucleotide of a predetermined sequence in a stepwise manner using reversibly 3'-blocked nucleoside triphosphates was described by Hiatt and Rose (U.S. Pat. No. 5,990,300). They disclose besides esters, ethers, carbonitriles, phosphates, phosphoramides, carbonates, carbamates, borates, sugars, phosphoramidates, phenylsulfenates, sulfates and sulfones also nitrates as reversible 3'-protecting group. The deprotection may be carried out by chemical or enzymatic means. There are neither synthesis procedures nor deprotection conditions and enzymatic incorporation data disclosed for the nitrate group. The claimed deblocking solution preferably contains divalent cations like $Co^{2+}$ and a biological buffer like Tris. 3'-Blocked nucleoside triphosphates containing a label are not disclosed.

Buzby (US 2007/0117104) discloses nucleoside triphosphates for SBS which are reversibly protected at the 3'-hydroxyl group and carry a label at the base. The label is connected via a cleavable linker such as a disulfide linker or a photocleavable linker. The linker consists of up to about 25 atoms. 3'-Protection group can be besides hydroxylamines, aldehydes, allylamines, alkenes, alkynes, alcohols, amines, aryls, esters, ethers, carbonitriles, phosphates, carbonates, carbamates, borates, sugars, phosphoramidates, phenylsulfanates, sulfates, sulfones and heterocycles also nitrates.

There is no disclosure on the synthesis of nitrate protected nucleotides, the deprotection conditions or enzymatic incorporation.

Reversibly blocked nucleotides are also described by Milton et al. (US 2007/0166705). Protecting groups are based on acetalic structures or acetal precursors. One preferred structure is azidomethyl which has been commercialized by Illumina. The modified nucleotides also include a label attached via a cleavable linker such as acid-labile, disulfide or photolabile structures.

These linker structures are also described by Milton et al. in US 2006/0160081. Acid-labile acetal-type or acetal-precursor type linkers as well as photolabile urethane bonded linkers are disclosed. Preferable deprotection reagents are phosphines like TCEP. For the attachment of the cleavable linker to the nucleobase an aminopropargyl residue is preferably used.

Barnes et al. (U.S. Pat. No. 7,057,026 B2) discloses that 3'-protecting group and label are cleaved under identical conditions.

The synthesis of nitrate modified nucleosides have been described for instance by R. Boschan et al., Chemical Reviews 1955, 55, 485, J. Honeyman et al., Sugar Nitrates in Advances in Carbohydrate Chemistry, ed. by M. L. Wolfromm and R. S. Tipson, Academic Press, New York, 1957, 12, 117-135, E. Naimi et al., J. Med. Chem. 2003, 46, 995, G. H. Hakimelahi et al., Helv. Chim. Acta 1984, 67, 906, J. Giziewicz et al., J. Org. Chem. 1999, 64, 2149, G.-F. Huang et al., J. Org. Chem. 1977, 42, 3821 or in DE 2160104 and in DE 2606532.

Deprotection conditions of the nitrate protecting group are reviewed by R. Boschan et al., Chemical Reviews 1955, 55, 485, J. Honeyman et al., Sugar Nitrates in Advances in Carbohydrate Chemistry, ed. by M. L. Wolfromm and R. S. Tipson, Academic Press, New York, 1957, 12, 117-135 or by T. W. Greene, Protective groups in organic synthesis, Wiley 1981, page 70-71. Nitrate esters can be cleaved by solvolytic decomposition via hydrolysis using alkaline conditions or sulfuric acid or by reductive conditions via electrolytic reduction, Grignard reagents, hydrazines, hydrogenolysis, lithium aluminium hydride, metal-acid mixtures, metals or anorganic sulfides like hydrogen sulfide and ammonium sulfide, ammonium hydrogen sulfide or sodium sulfide. Cleavage by irradiation is also described.

Organic sulfides are not described as deprotection reagent for nitrate esters. However, R. A. Yeates et al. (Molecular Pharmacology 1985, 28, 555) describe the reaction between organic nitrates and organic sulfhydryl compounds in the context of mechanism of action of nitroglycerin, only weakly concentrated sulfhydryl compound solutions were used. A similar context is described in M. Feelisch et al., European Heart Journal 1988, 9 (Suppl. A), 57-62.

B. Canard et al. (PNAS 1995, 92, 10859-10863) describe that 3'-esterified 2'-deoxynucleoside 5'-triphosphates are false chain-terminator substrates since DNA polymerases can incorporate them into DNA and subsequently use this new 3'-end to insert the next correctly paired dNTP after partial enzymatic cleavage of the ester group.

Addition of pyrophosphatase to polymerase catalyzed DNA synthesis reactions to eliminate pyrophosphate and improve DNA synthesis has been described in WO 94/05797 and US 2003/0134276. Its use in sequencing reactions is also described therein.

In US 2008/0138804 a composition comprising a mutated polymerase, manganese or magnesium salts, an organic solvent and an inorganic pyrophosphatase are disclosed in the context of sequencing.

Addition of Mn(II) ions to the Terminator II buffer for the incorporation of 3'-O-azidomethyl and 3'-O-allyl protected nucleoside triphosphates is described in J. Guo et al., PNAS 2008, 105, 9145-9150) and T. S. Kim et al., ChemBioChem 2010, 11, 75-78.

However, all these methods are sub-optimal with respect to performance with respect to quantitative enzymatic incorporation of the 3'-reversibly blocked nucleotide and fast and efficient deprotection as well as effective blockage property of the reversible 3'-protecting group. Due to residual esterase activities of DNA polymerases, the 3'-ester derived blockages known in the art are never 100% complete (Rasolonjatovo and Sarfati, Nuclosides & Nucleotides, 18 (4&5), 1021-1022, 1999).

Thus, there is a need in the art for a solution to provide deoxynucleosides which comprise a reversible but completely blocked 3' terminus.

SUMMARY OF THE INVENTION

In a first aspect, the present invention provides a deoxynucleoside tri- or tetraphosphate comprising a 3'-nitrate and a detectable label covalently bound to the oxygen atom of an oxymethyl or oxyallyl or oxypropargyl substitution of a nucleobase.

The label, for example may be a fluorescent label. The label may be connected to the base via a cleavable linker.

In a second aspect, the present invention is directed to the use of a deoxynucleoside tri- or tetraphosphate as disclosed above within a polymerase catalyzed DNA synthesis reaction. The DNA synthesis reaction may be performed in the presence of a pyrophosphatase.

In a third aspect, the present invention provides a kit comprising
 a DNA polymerase,
 a pyrophosphatase, and
 at least one deoxynucleoside tri- or tetraphosphate as disclosed above.

In a fourth aspect, the present invention provides a reaction mixture comprising
 a nucleic acid template with a primer hybridized to said template,
 a DNA polymerase,
 a pyrophosphatase, and
 at least one deoxynucleoside tri- or tetraphosphate as disclosed above.

In a fifth aspect, the present invention is based on the use of pyrophosphatase for stabilizing deoxynucleotide 3'-nitrate ester during and subsequent to a polymerase catalyzed DNA synthesis reaction.

In a sixth aspect, the present invention provides a method of performing a DNA synthesis reaction comprising the steps of
 preparing a reaction mixture by means of providing a nucleic acid template with a primer hybridized to said template, a DNA polymerase, at least one deoxynucleoside tri- or tetraphosphate as disclosed above, and
 subjecting said reaction mixture to conditions which enable a DNA polymerase catalyzed primer extension reaction.

Said DNA synthesis reaction may be a sequencing reaction.

In a seventh aspect, the present invention provides a method for analyzing a DNA sequence comprising the steps of
 a) providing a nucleic acid template with a primer hybridized to said template forming a primer/template hybridization complex,
 b) adding DNA polymerase and a labeled deoxynucleoside tri- or tetraphosphate as disclosed above, and a pyrophosphatase,
 c) subjecting said reaction mixture to conditions which enable a DNA polymerase catalyzed primer extension reaction,
 d) determining, whether said compound has been incorporated into said primer/template hybridization complex.

Such a method may further comprise the steps of
 e) removing said blocking group and optionally said label from said complex, and
 f) repeating steps b) to e) at least once.

Thus it is possible that a different labeled deoxynucleoside tri- or tetraphosphate compound is always added during repeat of step b). For example, steps b) to e) can be repeated at least 4 times and wherein 4 different labeled deoxynucleoside tri- or tetraphosphate compounds representing A, G, C and U are used.

In one embodiment, step e) is performed by means of adding a sulfide or a mercaptane.

BRIEF DESCRIPTION OF FIGURES

FIG. 1 Schematic drawing of the synthesis of a 3'-nitrate-2'-deoxynucleoside-5'-triphosphate disclosed in example 1

FIG. 2 Schematic drawing of the NHS ester of a detectable label according to example 2

FIG. 3 Schematic drawing of the synthesis a labeled 3'-nitrate-2'-deoxynucleoside-5'-triphosphate disclosed in example 2

FIG. 4 Concept of the primer extension experiment disclosed in example 3 using a primer according to Seq. ID. No: 1 and a template according to Seq. Id. No: 2, resulting in an extended primer according to Seq. ID No: 3

FIG. 5 Cleavage of the 3'-nitrate group prior to incorporation into a nascent DNA strand according to example 4

DETAILED DESCRIPTION OF THE INVENTION

Definitions

The term "nucleic acid" generally refers to both DNA or RNA, whether it is a product of amplification, synthetically created, products of reverse transcription of RNA or naturally occurring. Typically, nucleic acids are single- or double-stranded molecules and are composed of naturally occurring nucleotides. Double-stranded nucleic acid molecules can have 3'- or 5'-overhangs and as such are not required or assumed to be completely double-stranded over their entire length. Furthermore, the nucleic acid can be composed of non-naturally occurring nucleotides and/or modifications to naturally occurring nucleotides. Examples are listed herein, but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; phosphorothioate, methylphosphonates, phosphoroamidates and phosphotriester linkages between nucleotides to prevent degradation; methylation; and modified bases or nucleosides such as deoxy-inosine, 5-bromo-dU, 2'-deoxy-uridine, 2-aminopurine, 2',3'-dideoxy-cytidine, 5-methyl-dC, locked nucleic acids (LNA's), iso-dC and -dG bases, 2'-O-methyl RNA bases and fluorine modified nucleosides.

The term "complementary" generally refers to the ability to form favorable thermodynamic stability and specific pairing between the bases of two nucleotides at an appropriate temperature and ionic buffer conditions. This pairing is dependent on the hydrogen bonding properties of each nucleotide. The most fundamental examples of this are the hydrogen bond pairs between thymine/adenine and cytosine/guanine bases. In the present invention, primers for amplification of target nucleic acids can be both fully complementary over their entire length with a target nucleic acid molecule or "semi-complementary" wherein the primer contains an additional, non-complementary sequence minimally capable or incapable of hybridization to the target nucleic acid.

The term "hybridize" generally refers to the base-pairing between different nucleic acid molecules consistent with their nucleotide sequences. The terms "hybridize" and "anneal" can be used interchangeably.

The term "oligonucleotide" generally refers to a nucleic acid sequence typically designed to be single-stranded DNA and less than 75 nucleotides in length.

The term "primer" generally refers to an oligonucleotide that is able to anneal, or hybridize, to a nucleic acid sequence and allow for extension under sufficient conditions (buffer, dNTP's, polymerase, mono- and divalent salts, temperature, etc. . . . ) of the nucleic acid to which the primer is complementary.

The terms "template nucleic acid", "template molecule", "target nucleic acid", and "target molecule" can be used interchangeably and refer to a nucleic acid molecule that is the subject of an amplification reaction that may optionally be interrogated by a sequencing reaction in order to derive its sequence information. The template nucleic acid may be a nucleic acid which has been generated by a clonal amplification method and which may be immobilized on a solid surface, i.e. immobilized on beads or an array.

The term "nucleoside" refers to a compound consisting of a base linked to the C-1' carbon of a sugar, for example, ribose or deoxyribose. The base portion of the nucleoside is usually a heterocyclic base, e.g., a purine or pyrimidine.

The term "nucleotide" refers to a phosphate ester of a nucleoside, as a monomer unit or within a polynucleotide. "Nucleoside 5'-triphosphate" refers to a nucleotide with a triphosphate ester group attached to the sugar 5'-carbon position, and is sometimes denoted as "NTP", "dNTP" (2'-deoxynucleoside triphosphate or deoxynucleoside triphosphate) and "ddNTP" (2',3'-dideoxynucleoside triphosphate or dideoxynucleoside triphosphate). "Nucleoside 5'-tetraphosphate" refers to an alternative activated nucleotide with a tetraphosphate ester group attached to the sugar 5'-carbon position.

The term "label" in its broadest sense, refers to any moiety or property that is detectable, or allows the detection of that which is associated with it. For example, a nucleotide, oligo- or polynucleotide that comprises a label is detectable. Ideally, a labeled oligo- or polynucleotide permits the detection of a hybridization complex, particularly after a labeled nucleotide has been incorporated by enzymatic means into said hybridization complex of a primer and a template nucleic acid. A label may be attached covalently or non-covalently to a nucleotide, oligo- or polynucleotide. In various aspects, a label can, alternatively or in combination: (i) provide a detectable signal; (ii) interact with a second label to modify the detectable signal provided by the second label, e.g., FRET; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior. Labels vary widely in their structures and their mechanisms of action. Examples of labels include, but are not limited to, fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes of the fluorescein family, dyes of the rhodamine family, dyes of the cyanine family, or a coumarine, an oxazine, a boradiazaindacene or any derivative thereof. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), Texas Red is commercially available from, e.g., Life Technologies (Molecular Probes, Inc.) (Grand Island, N.Y.). Dyes of the cyanine family include, e.g., CY2, CY3, CY5, CY5.5 and CY7, and are commercially available from, e.g., GE Healthcare Life Sciences (Piscataway, N.J., USA).

Embodiments of the Invention

The present invention first of all provides a deoxynucleoside tri- or tetraphosphate comprising a 3'-nitrate and a detectable label covalently bound to the oxygen atom of an oxy methyl or oxy allyl or oxypropargyl substitution of a nucleobase. The synthesis of such a compound relies on chemical methods known in the art. Two examples are disclosed in detail in examples 1 and 2 below.

In a first step, a 3'-O-nitro-nucleoside triphosphate may be generated by means of first reacting an anhydro-nucleobase such as anhydro-thymidine with ammonium nitrate. Subsequently, said 3'-O-nitro-nucleobase is changed into a respective 3'-O-nitro-nucleobase-triphosphate in the form of a tetrasodium salt by means of reacting it with phosphoryl chloride and subsequently with pyrophosphate.

Alternatively, prior to the synthesis of a triphosphate, a reactive moiety may be incorporated into the base, such that subsequent to the generation of the triphosphate, the detectable label can be added to the base. The advantage is that a detectable label is not subject to any undesired side reactions during the reaction with phosphoryl chloride. For example, a 3'-O-nitro-nucleobase may be reacted with a silyl chloride in order to generate a 5'-O-silyl-3'-O-nitro-nucleobase. Subsequently, a linker containing a trifluoroacetyl-protected amino group and a disulfide linkage is incorporated into the base. Subsequent to the generation of the triphosphate with phosphoryl chloride and pyrophosphate, the protective group is removed and the compound can be labeled with the NHS-ester form of a detectable label.

The deoxynucleoside tri- or tetraphosphate may contain any nucleobase known in the art. Preferable are nucleobases which are conventionally used in DNA sequencing methods. For example said nucleobases can be adenine, 7-deazaadenine, guanine, 7-deazaguanine, cytosine, thymine or uracil.

The label can be any label. Preferably, said detectable label is selected from a group consisting of mass-tag, color label, e-tag and a hapten which is detectable by an antibody. Highly preferred is a fluorescent label, since fluorescent labels can be used for sequence by synthesis methods. Said fluorescent label can be but are not limited to a fluorescein, a rhodamine, a cyanine, a coumarine, an oxazine, a boradiazaindacene or any derivative thereof.

For sequencing by synthesis applications, it is desirable that the labels of the deoxynucleoside tri- or tetraphosphate as disclosed are connected to the base via a cleavable linker. For example said label may be connected to the base via a disulfide bridge or an ester bridge. If the label is covalently bound via a cleavable linker comprising a disulfide bond, said linker may have the structure base-A—O—CH2-S—S-L-label, wherein A is —CH2-, —CH=CH—CH2- or —C≡C—CH2-,
A-O— belongs to the substitution of the nucleobase, and
L is a chain of 4-200 carbon atoms optionally comprising moieties selected from —O—, —NR—, —S—, NRC(=X)—, —(X=)CNR—, —NRC(=X)—NR—, —NRC(=X)—O—, —OC(=X)—NR—, —O—POH(=O)O—, —S(=O)2-, —S(=O)2NR—, —NR—S(=O)2-, with R=H, Me, and X=O, S.

The label may also be connected as follows:

base-A—O—C(=O)—CH2-L-label, wherein

A is —CH2-, —CH═CH—CH2- or —C≡C—CH2-

L is a chain of 4-200 carbon atoms optionally comprising moieties selected from —O—, —NR—, —S—, NRC(═X)—, —(X═)CNR—, —NRC(═X)—NR—, —NRC(═X)—O—, —OC(═X)—NR—, —O—POH(═O)O—, —S(═O)2-, —S(═O)2NR—, —NR—S(═O)2-, with R═H, Me, and X═O, S.

In one embodiment of the invention, the base of the deoxynucleoside tri- or tetraphosphate is a uracil or cytosine. In this case, the label is preferably connected to the C5 position of the base. In another embodiment, said base is a 7-deazaadenine or 7-deazaguanine. Then, the label is preferably connected to the C7 position of the base. In a further embodiment, said base is an adenine or a guanine. Then, said structure is connected to the C8 position of the base.

The newly provided deoxynucleoside tri- or tetraphosphates are very well suited for use as building blocks for any polymerase catalyzed DNA synthesis reaction, including but not limited to sequencing reactions.

In this context, it has been proven to be advantageous, if such a DNA synthesis reaction is performed in the presence of pyrophosphatase. The inventors have observed that in the absence of pyrophosphatase, the 3'-O-nitro blocking group may have sub-optimal stability in some cases. As a consequence, undesired incorporation of more than one building block at a time may occur. Yet, this observed effect is completely avoided in the presence of pyrophosphatase.

The reason for this surprising effect is not completely understood. The hydrolysis of inorganic pyrophosphate (PPi) to two phosphate ions typically renders reactions effectively irreversible, since this process is highly exergonic. In the context of the present invention, however, such additional stabilization effect has been proven. The presence of inorganic pyrophosphatase during a primer extension reaction and in particular during a DNA sequencing reaction results in stabilized formation of a completely 3'-protected-incorporation product. In particular, the presence of inorganic pyrophosphatase leads to a stabilized formation of a 3'-nitrate protected incorporation product with less side-reactions.

Preferably, such a polymerase catalyzed DNA synthesis reaction is a primer extension reaction. Most preferably, it is a DNA sequencing reaction. However, said reaction may also be a terminal transferase reaction, characterized in that the activity of the polymerase is independent from a primer/template complex.

It is obvious that all these reactions comprise the step of removing said 3'-nitrate blocking group. This removal may be achieved, for example by means of adding a sulfide or a mercaptane, which is preferably cysteamine or cysteine, most preferably cysteamine. Trace amounts of these types of compounds even do not interfere with subsequent DNA synthesis steps. An advantage of using organic sulfide reagents like cysteamine or cysteine is that these compounds are almost odorless and less toxic compared to inorganic sulfides, and they are highly soluble in aqueous media.

In several sequencing by synthesis formats, it is highly advantageous, if the detectable label is removed. Thus, the present invention also provides a use of the inventive compounds, which comprises the step of removing said detectable label in step e) either before or after the removal of the 3'-blocking group or simultaneously to the removal of the blocking group subsequent to incorporation of the respective nucleotide building block into the nascent nucleotide chain.

In one embodiment, the steps of removing said 3'-nitrate blocking group and removing said detectable label are performed simultaneously. Preferably removal of said 3'-nitrate and removal of said detectable label are achieved by identical means. For example, the 3'-nitrate blocking group and the detectable label may be chemically removed simultaneously by means of adding a compound selected from the group of sulfides and mercaptanes, or by mixtures of sulfides or mercaptanes with compounds selected from the group of amines, hydrazines, hydroxylamines or hydroxides.

The present invention also provides kits for performing DNA synthesis reactions and in particular DNA sequencing reactions as disclosed above.

Such a kit may comprise
  a DNA polymerase,
  a pyrophosphatase, and
  at least one deoxynucleoside tri- or tetraphosphate disclosed above.

The DNA polymerase may be any DNA dependent DNA polymerase. Preferably, such a polymerase is a polymerase with high fidelity, i.e. a polymerase which possesses a 3'-5' exonuclease proofreading activity and therefore provides a very low degree of nucleotide misincorporations. Prominent examples are DNA polymerase I, Klenow fragment or Therminator™ II DNA Polymerase (New England Biolabs).

Pyrophosphatases are enzymes that catalyze the conversion of one molecule of pyrophosphate to two phosphate ions. Several inorganic pyrophosphatases are commercially available (e.g. Roche Applied Science Catalog Number: 10150681103). The surprising stabilization effect in the context the present invention is disclosed above.

In view of this effect, the present invention in addition provides a reaction mixture comprising
  a nucleic acid template with a primer hybridized to said template,
  a DNA polymerase,
  a pyrophosphatase, and
  at least one deoxynucleoside tri- or tetraphosphate as disclosed above.

It seems, that solutions of pure nucleoside triphosphates comprising 3'-nitrate blocking group are rather stable and do not benefit from addition of any stabilizing agent. Instead, the stabilizing effect of pyrophosphatase occurs predominantly during a DNA synthesis reaction. Thus pyrophosphatase may be used for stabilizing deoxynucleotide 3'-nitrate ester during and subsequent to a polymerase catalyzed DNA synthesis reaction. Preferably, pyrophosphatase is accordingly used during a primer extension reaction or a sequencing reaction.

The new 3' O-nitro-nucleoside triphosphates are particularly useful for DNA synthesis reaction. Typically, such DNA synthesis reactions are comprising the steps of
  a) preparing a reaction mixture by means of providing a nucleic acid template with a primer hybridized to said template, a DNA polymerase, at least one deoxynucleoside tri- or tetraphosphate as disclosed above, and
  b) subjecting said reaction mixture to conditions which enable a DNA polymerase catalyzed primer extension reaction.

Such a method may be a sequencing reaction. Depending on the instrument platform that is being used, there exist many different embodiments to perform a respective sequencing analysis. In particular, the present invention enables for a method for analyzing a DNA sequence comprising the steps of
  a) providing a nucleic acid template with a primer hybridized to said template forming a primer/template hybridization complex,
  b) adding DNA polymerase, and a deoxynucleoside tri- or tetraphosphate comprising a 3'-nitrate and a detectable label covalently bound to the oxygen atom of an oxymethyl or oxyallyl or oxypropargyl substitution of a nucleobase, c) subjecting said reaction mixture to conditions which enable a DNA polymerase catalyzed primer extension reaction, d) determining, whether said compound has been incorporated into said primer/template hybridization complex.

Preferably, the said detectable label is a fluorescent label. Subsequent to it incorporation, an excitation of the label may be achieved by any means available in the art, for example by a LED or an array of LEDs positioned in optical connection to an array of reaction wells in which the sequencing reactions take place. Subsequently, fluorescence emission can for example be detected by a CCD camera which is appropriately positioned either above or below.

Also preferably, the fluorescent label may be connected to the base via a cleavable linker. Alternatively, the incorporated fluorescent label may be bleached such that it does not interfere with subsequent detection events when the nascent nucleotide chain is further elongated.

In addition, the presence of pyrophosphatase during or subsequent to the incorporation event may stabilize the 3'-blocking group to the extent necessary.

The sequencing reaction may further comprise the steps of e) removing said blocking group and optionally said label from said complex, and f) repeating steps b) to e) at least once.

If pyrophosphatase has been applied, it needs to be removed preferably directly after step c).

Addition and removal of reagents and fluids may be enabled by any conventional fluidic means known in the art. Wash steps may be applied between the steps as appropriate, if the template nucleic acid is immobilized on a solid surface.

Since nucleic acids are typically composed out of different nucleotide residues, different labeled deoxynucleoside tri- or tetraphosphate compounds are added during repeat of step b). Therefore steps b) to e) are repeated at least 4 times and 4 different labeled deoxynucleoside tri- or tetraphosphate compounds representing A, G, C and T or A, G, C and U are used. However, it is not necessary that all 4 building blocks are always provided in the same order. It is even within the scope of the present invention, if the order of providing the different building blocks is being changed during the sequencing process. If different labels are used for the four different deoxynucleoside tri- or tetraphosphates all four deoxynucleoside tri- or tetraphosphates (A, G, C, T/U) may be applied as a mixture simultaneously in each step b).

In any case, step e), i.e. removing said 3'-nitrate blocking group from said complex is required to obtain a sequencing run and determine multiple nucleotide residues in a row. For example, step e) is efficiently performed by means of adding a sulfide or a mercaptane, which are known to resolve nitrate ester bonds. For example, step e) is performed by means of adding a cysteamine or cysteine compound.

Preferably, step e) also comprises the step of removing said label from said complex. In such an embodiment, the label, which may be a fluorescent label is being connected to the nucleobase via a cleavable linker. Preferably, said linker is selected in such a way that removal of the 3'-nitrate and the detectable label is achieved by identical means. In this regard, sulfides and mercaptanes are chemical agents which are capable of cleaving a broad variety of different potential linker structures, containing in particular disulfide and ester linkages.

EXAMPLES

Example 1

Synthesis of 3'-O-nitro-β-D-thymidine 5'-triphosphate (3)

3'-O-Nitro-β-D-thymidine (2)

The synthesis of compound 2 followed a procedure similar to E. Naimi et al., J. Med. Chem. 2003, 46, 995-1004, but without the temporary protection of the 5'-hydroxyl group. 2,3'-Anhydrothymidine 1 was prepared according to M. I. Balagopala, A. et al., Nucleosides and Nucleotides 1996, 15, 899-906. 2,3'-Anhydrothymidine 1 (11.5 g, 51.3 mmol) and ammonium nitrate (61.6 g, 769 mmol) were dissolved in 328 mL of dry N,N-dimethylformamide and heated at 110° C. three times for 8 hours with overnight stirring at room temperature in between. Then, the solvent of the dark brown reaction mixture was evaporated under reduced pressure. The oily residue was dissolved in ethyl acetate and water and washed twice with water. Re-washing of the aqueous phases with ethyl acetate was necessary. The combined organic layers were dried over $Na_2SO_4$ and evaporated. The oily residue was then taken up in methanol and $SiO_2$ was added. The mixture was evaporated to dryness yielding a brown powder and the crude product was finally purified by flash column chromatography on $SiO_2$ with hexane/ethyl acetate (60/40 to 0/100) as eluent (dry-load).

Yield: 3.45 g (12.0 mmol) of 2 as brownish solid (23%) after lyophilization from 1,4-dioxane.

TLC ($SiO_2$; 10% methanol in dichloromethane): $R_f$=0.61.

ESI-MS (m/z): $[M-H]^-$ calcd for $C_{10}H_{13}N_3O_7$, 286.23. found 286.03.

$^1$H-NMR ($d_6$-DMSO): 1.79 (s, 3H), 2.40-2.50 (m, 2H), 3.68 (m, 2H), 4.19 (m, 1H), 5.31 (t, 1H), 5.60 (m, 1H), 6.15 (dd, 1H), 7.73 (s, 1H), 11.34 (s, 1H).

3'-O-Nitro-β-D-thymidine 5'-triphosphate, tetrasodium salt (3)

3'-O-Nitro-β-D-thymidine 2 (100 mg, 0.348 mmol) was coevaporated with dry pyridine and then dissolved in 4 mL of dry trimethylphosphate. The solution was cooled to 0° C. and dry pyridine (334 µL, 4.18 mmol) was added. Then, phosphoryl chloride (97 µL, 1.04 mmol, diluted with 97 µL of dry trimethylphosphate) was added dropwise to the solution. After stirring for 10 minutes at 0° C. tributylamine (340 µL, 1.40 mmol) and Tributylammonium pyrophosphate (6.96 mL, 3.48 mmol, 0.5 M in dry N,N-dimethylformamide) were added slowly and simultaneously to the reaction mixture. After a reaction time of further 10 minutes it was quenched with 10 mL of 1.0 M triethylammonium bicarbonate solution (pH 8) and allowed to warm to room temperature. The volatile solvents were evaporated under reduced pressure. Reaction control was performed via analytical anion-exchange chromatography and via LC-ESI mass spectrometry. The crude product was purified by semi-preparative anion-exchange chromatography applying a gradient of triethylammonium bicarbonate (pH 8) as eluent. Fractions containing 3 (triethylammonium salt) were pooled and the solvent was evaporated. The residue was coevaporated three times with water and dissolved in 1.0 mL of water. Finally, the product was transferred into its sodium salt by cation-exchange chromatography. Fractions containing 3 (sodium salt) were pooled, the solvent was evaporated and the residue was dissolved in 1.0 mL of water (PCR grade). The yield of the triphosphate was determined by UV spectroscopy at 260 nm using the extinction coefficient of the unmodified thymidine nucleotide: $\epsilon$=9300 $M^{-1}$ $cm^{-1}$.

Yield: 60.7 µmol (60.7 µmol/mL) of 3 (17%) over 3 steps.

ESI-MS (m/z): $[M-H]^-$ calcd for $C_{10}H_{16}N_3O_{16}P_3$ (protonated form), 526.17. found 527.00.

$^1$H-NMR ($D_2O$): 1.88 (s, 3H), 2.50-2.60 (m, 2H), 4.19-4.30 (m, 2H), 4.48 (m, 1H), 5.78 (m, 1H), 6.30 (t, 1H), 7.73 (s, 1H).

$^{31}$P-NMR ($D_2O$): −21.58 (t), −11.38 (d), −5.80 (d).

Example 2

Synthesis of MR121-labelled 3'-O-nitro-2'-deoxy-β-D-uridine 5'-triphosphate (13)

Synthesis of MR121-PEG4-NHS (6)

MR121-PEG$_4$-COOH (5)

MR121-NHS 4 was synthesized according to EP 0747447. MR121-NHS 4 (36.9 mg, 61.1 µmol) was dissolved in 4 mL of 1,4-dioxane. 15-Amino-4,7,10,13-tetraoxa-pentanoic acid (Thermo Scientific, CA-PEG$_4$, 24.3 mg, 91.7 µmol, dissolved in 1 mL of water) was dropped into the solution. Then, sodium hydrogen carbonate (15.4 mg, 183.3 µmol, dissolved in 1 mL of water) was added to the reaction mixture. After stirring for 2 hours at room temperature the dark blue solution was diluted with dichloromethane and a suspension was obtained. Methanol was added dropwise to the suspension to increase the polarity of the organic solvent in order to obtain a clear blue solution. The organic layer was washed twice with 10% aqueous citric acid/saturated sodium chloride solution (1/1, v/v) and once with saturated sodium chloride solution. Re-washing of the aqueous phases with dichloromethane was necessary. The combined organic layers were dried over $Na_2SO_4$ and evaporated. The crude product was purified by flash column chromatography on $SiO_2$ with dichloromethane/methanol/acetic acid (94.9/5/0.1 to 69.9/30/0.1) as eluent. Fractions containing the pure product were combined and evaporated. The remaining residue was dissolved in acetonitrile and $SiO_2$ was filtered off. The pure product 5 was isolated as perchlorate salt.

Yield: 43.7 mg (58.0 µmol) of 5 (95%) as dark blue solid.

TLC ($SiO_2$; 8% methanol, 0.1% acetic acid in dichloromethane): $R_f$=0.44.

ESI-MS (m/z): $[M]^+$ calcd for $C_{35}H_{49}N_4O_8^+$ (cation) 653.80. found 653.01.

MR121-PEG$_4$-NHS (6)

MR121-PEG$_4$-COOH 5 (28.0 mg, 37.2 µmol) was dissolved in 2 mL of dry dichloromethane. N-Hydroxysuccinimide (4.7 mg, 40.9 µmol) and N-ethyl-N'-(3-dimethylaminopropyl)carbodiimide hydrochloride (8.5 mg, 44.6 µmol) were added to the solution. After stirring at room temperature for 2 hours, further portions of N-hydroxysuccinimide (2.4 g, 20.4 µmol) and N-ethyl-N'-(3-dimethylaminopropyl)carbodiimide hydrochloride (4.3 mg, 22.3 µmol) were added. Stirring was continued for further 2 hours at room temperature and the solution was then diluted with dichloromethane. The organic layer was washed twice with 10% aqueous citric acid/saturated sodium chloride solution (1/1, v/v) and once with saturated sodium chloride solution. Re-washing of the aqueous phases with dichloromethane was necessary. The combined organic layers were dried over $Na_2SO_4$ and evaporated. The crude product was purified by flash column chromatography on $SiO_2$ with dichloromethane/methanol/acetic acid (94.8/5/0.2 to 89.8/10/0.2) as eluent, and isolated as perchlorate salt after evaporation of the pooled product fractions.

Yield: 16.2 mg (19.1 µmol) of 6 (51%) as dark blue solid.

TLC ($SiO_2$; 8% methanol, 0.1% acetic acid in dichloromethane): $R_f$=0.56.

ESI-MS (m/z): $[M]^+$ calcd for $C_{39}H_{52}N_5O_{10}^+$ (cation) 750.87. found 750.01.

5'-O-(tert-Butyldimethylsilyl)-3'-O-nitro-β-D-thymidine (7)

3'-O-Nitro-β-D-thymidine 2 (3.25 g, 11.3 mmol) was coevaporated three times with dry pyridine and then dissolved in 32.5 mL of dry pyridine. Then, tert-butyldimethylsilyl chloride (2.56 g, 17.0 mmol) and 4-(dimethylamino)pyridine (2.07 g, 17.0 mmol) were added. After stirring for 20 hours at room temperature the solvent was evaporated and the oily residue was coevaporated with toluene. Compound 7 was purified by flash column chromatography on $SiO_2$ with dichloromethane/methanol (100/0 to 97/3) as eluent.

Yield: 4.01 g (10.0 mmol) of 7 as white solid (88%) after lyophilization from 1,4-dioxane.

TLC ($SiO_2$; 3% methanol in dichloromethane): $R_f$=0.48.

ESI-MS (m/z): $[M-H]^-$ calcd for $C_{16}H_{27}N_3O_7Si$, 400.50. found 399.97.

$^1$H-NMR ($CDCl_3$): 0.15 (s, 6H), 0.95 (s, 9H), 1.91 (s, 3H), 2.24 (m, 1H), 2.57 (dd, 1H), 3.95 (m, 2H), 4.24 (m, 1H), 5.47 (d, 1H), 6.32 (m, 1H), 7.47 (s, 1H), 9.23 (s, 1H).

5'-O-(tert-Butyldimethylsilyl)-3'-O-nitro-5-(hydroxymethyl)-2'-deoxy-β-D-uridine (8)

The bromination of compound 7 and the subsequent hydrolysis followed a route similar to the literature (M. Münzel et al., Angew. Chem. Int. Ed. 2010, 49, 5375-5377; J. Matulic-Adamic et al., Chem. Pharm. Bull. 1998, 36, 1554-1557). A suspension of compound 7 (5.59 g, 13.9 mmol), N-bromosuccinimide (2.85 g, 16.0 mmol), and 2,2'-azobis(2-methylpropionitrile) (457 mg, 2.78 mmol) in 230 mL of dry α,α,α-trifluorotoluene was heated at 80° C. for 30 minutes. The solvent of the orange solution was then evaporated under reduced pressure. The oily residue was suspended in 56 mL of water/tetrahydrofuran (1/1, v/v) and sodium hydrogen carbonate (1.04 g, 12.3 mmol) was added. After stirring for 2.5 hours at room temperature the solvent was evaporated. The residue was dissolved in dichloromethane and extracted twice with saturated sodium bicarbonate solution. The organic layers were dried over $Na_2SO_4$ and evaporated. The crude product including a significant amount of starting material was purified by flash column chromatography on $SiO_2$ with hexane/ethyl acetate (60/40 to 40/60) as eluent.

Yield: 1.63 g (3.90 mmol) of 8 over 2 steps as white solid (28% or 50% based on recovered starting material) after lyophilization from 1,4-dioxane.

TLC ($SiO_2$; 5% methanol in dichloromethane): $R_f$=0.39.

ESI-MS (m/z): $[M-H]^-$ calcd for $C_{16}H_{27}N_3O_8Si$, 416.49. found 416.78.

$^1$H-NMR ($CDCl_3$): 0.14 (s, 6H), 0.94 (s, 9H), 1.57 (s, 3H), 2.21-2.29 (m, 1H), 2.56-2.63 (m, 2H), 3.90-3.99 (m, 2H), 4.26 (m, 1H), 4.40 (m, 2H), 5.48 (d, 1H), 6.28 (dd, 1H), 7.68 (s, 1H), 8.42 (s, 1H).

5'-O-(tert-Butyldimethylsilyl)-3'-O-nitro-5-{[methylthio)methoxy]methyl}-2'-deoxy-β-D-uridine (9)

The modification of the 5-hydroxymethyl group was carried out similar to a note in the literature (K. Suzuki et al., Chem. Lett. 1979, 1277-1278). Compound 8 (2.14 g, 5.11 mmol) and silver nitrate (1.04 g, 6.14 mmol) were suspended in 22 mL of dry toluene. Chloromethyl methyl sulfide (600 µL, 7.16 mmol) and dry triethylamine (998 µL, 7.16 mmol) were slowly dropped into the solution. After stirring for 2 hours at 45° C. the reaction mixture was filtered and the filtrate was evaporated. The crude product including a significant amount of starting material was purified by flash column chromatography on $SiO_2$ with hexane/ethyl acetate 70/30 to 40/60 as eluent.

Yield: 645 mg (1.35 mmol) of 9 as white foam or yellowish oil (26% or 54% based on recovered starting material).

TLC ($SiO_2$; 3% methanol in dichloromethane): $R_f$=0.46.

ESI-MS (m/z): $[M-H]^-$ calcd for $C_{18}H_{31}N_3O_8SSi$, 476.61. found 475.91.

$^1$H-NMR ($CDCl_3$): 0.14 (s, 6H), 0.92 (s, 9H), 2.18 (s, 3H), 2.22-2.30 (m, 1H), 2.62 (dd, 1H), 3.95 (m, 2H), 4.26 (m, 1H), 4.31 (s, 2H), 4.71 (s, 2H), 5.49 (d, 1H), 6.26 (dd, 1H), 7.68 (s, 1H), 9.62 (s, 1H).

5'-O-(tert-Butyldimethylsilyl)-3'-O-nitro-5-{[(N-trifluoroacetyl-2-aminoethyl)dithiomethoxy]methyl}-2'-deoxy-β-D-uridine (10) and 3'-O-Nitro-5-{[(N-trifluoroacetyl-2-aminoethyl)dithiomethoxy]methyl}-2'-deoxy-β-D-uridine (11)

The synthesis of compound 11 followed a strategy described in the literature (J. Guo et al., Proc. Natl. Acad. Sci. USA 2008, 105, 9145-9150; A. Semenyuk et al., J. Am. Chem. Soc. 2006, 128, 12356-12357. Compound 9 (50.0 mg, 0.105 mmol) was dissolved in 550 µL of dry dichloromethane and triethylamine (14.6 µL, 0.105 mmol, diluted with 50 µL of dry dichloromethane) was dropped into the solution. After stirring for 30 minutes at room temperature the solution was cooled to 0° C. Then, sulfuryl chloride (12.8 µL, 0.158 mmol, diluted with 75 µL of dry dichloromethane) was added dropwise into the cold solution in two portions over a period of 45 minutes. Afterwards, the solution was slowly warmed to room temperature and stirring was continued for another 45 minutes. Then, potassium p-toluenethiosulfonate (35.7 mg, 0.158 mmol, dissolved in 50 µL of dry N,N-dimethylformamide) was added and the reaction mixture was stirred for 1 hour. Finally, 2-(trifluoroacetamido)ethanethiol (54.5 mg, 0.315 mmol, dissolved in 100 µL of dry N,N-dimethylformamide), which was prepared according to M. J. Robins et al., J. Med. Chem. 2010, 53, 6040-6053, was dropped into the solution in two portions over a period of 1 hour. Stirring was further continued for another hour. Then, the solvent was evaporated under reduced pressure. The crude product containing compound 10 and 11 was purified by flash column chromatography on $SiO_2$ with dichloromethane/methanol (100/0 to 98.5/0.5) as eluent.

Yield: 11.9 mg (18.7 µmol) of 10 (18%) over 3 steps and 15.9 mg (30.5 µmol) of 11 (29%) over 4 steps as white foams.

TLC ($SiO_2$; 5% methanol in dichloromethane): $R_f$=0.70 (10) and 0.41 (11).

ESI-MS (m/z): $[M-H]^-$ calcd for $C_{21}H_{33}F_3N_4O_9S_2Si$, 633.73. found 633.04 (10) and $[M-H]^-$ calcd. for $C_{15}H_{19}F_3N_4O_9S_2$, 519.46. found 518.99 (11).

$^1$H-NMR ($CDCl_3$): 0.31 (s, 6H), 0.96 (s, 9H), 2.23-2.31 (m, 1H), 2.63-2.68 (m, 1H), 2.90-3.05 (m, 2H), 3.72-3.77 (m, 2H), 3.93-4.02 (m, 2H), 4.24-4.41 (3m, 3H), 4.91-4.99 (dd, 2H), 5.49 (d, 1H), 6.27 (dd, 1H), 7.64 (m, 1H), 7.84 (s, 1H), 8.79 (s, 1H) (10).

$^1$H-NMR ($CDCl_3$): 2.53-2.65 (m, 2H), 2.98 (t, 2H), 3.11 (m, 1H), 3.73 (m, 2H), 3.98 (dd, 2H), 4.28 (m, 1H), 4.34 (s, 2H), 4.96 (s, 2H), 5.62 (m, 1H), 6.21 (dd, 1H), 7.36 (t, 1H), 7.95 (s, 1H), 8.92 (s, 1H) (11).

3'-O-Nitro-5-{[(2-aminoethyl)dithiomethoxy]methyl}-2'-deoxy-β-D-uridine 5'-triphosphate, tetrasodium salt (12)

Compound 11 (14.6 mg, 28.1 µmol) was coevaporated with dry pyridine and then dissolved in 300 µL of dry trimethylphosphate. The solution was cooled to 0° C. and dry pyridine (27.0 µL, 0.337 mmol) was added. Then, phosphoryl chloride (7.8 µL, 84.3 µmol, diluted with 7.8 µL of dry trimethylphosphate) was added dropwise to the solution. After stirring for 15 minutes at 0° C. tributylamine (27.5 µL, 0.115 mmol) and tetrabutylammonium pyrophosphate (562 µL, 0.281 mmol, 0.5 M in dry N,N-dimethylformamide) were added slowly and simultaneously to the reaction mixture. After a reaction time of further 15 minutes it was quenched with 1 mL of triethylammonium bicarbonate solution (2.0 M in water; pH 8) and allowed to warm to room temperature. The volatile solvents were evaporated under reduced pressure. Reaction control was performed via analytical anion-exchange chromatography and via LC-ESI mass spectrometry. The crude product was purified by semi-preparative anion-exchange chromatography using a gradient of triethylammonium bicarbonate (pH 8) as eluent. Fractions containing the triphosphate were pooled and the solvent was evaporated. The residue was coevaporated three times with water yielding a small amount of 12 (triethylammonium salt), but mainly the corresponding triphosphate with the intact trifluoroacetyl protecting group. To promote complete cleavage of the protecting group the residue was dissolved in 2 mL of 25% aqueous ammonia. The reaction was followed by analytical anion-exchange chromatography. After 60 minutes at room temperature the solution was evaporated and the crude triphosphate 12 was purified by semi-preparative reversed-phase chromatography using 0.1 M triethylammonium acetate (pH 7.0)/acetonitrile gradient as eluent. Fractions containing 12 (triethylammonium salt) were pooled and the solvent was evaporated. The residue was coevaporated three times with water and dissolved in 1 mL of water. Finally, the product solution was transferred into its sodium salt by cation-exchange chromatography. Fractions containing 12 (sodium salt) were pooled, the solvent was evaporated and the residue was dissolved in 1.0 mL of water (PCR grade). The yield of the triphosphate was determined by UV spectroscopy at 260 nm using the extinction coefficient of an aminomodifier C6-dT: $\epsilon$=8400 $M^{-1}$ $cm^{-1}$.

Yield: 3.58 µmol (3.58 µmol/mL) of 12 (13%) over 4 steps.

ESI-MS (m/z): $[M-H]^-$ calcd for $C_{13}H_{23}N_4O_{17}P_3S_2$ (protonated form), 663.39. found 662.65.

$^1$H-NMR ($D_2O$): 2.49-2.65 (m, 2H), 3.05 (t, 2H), 3.34 (t, 2H), 4.24-4.30 (m, 2H), 4.25-4.30 (m, 3H), 4.96 (s, 2H), 5.81 (d, 1H), 6.34 (dd, 1H), 9.10 (s, 1H).

$^{31}$P-NMR ($D_2O$): -21.96 (t), -11.41 (d), -6.61 (d).

Synthesis of MR121-labelled 3'-O-Nitro-2'-deoxy-β-D-uridine triphosphate (13)

Compound 12 (250 nmol, lyophilized) was dissolved in 83.3 µL of aqueous sodium borate buffer (0.1 M, pH 8.5). Compound 6 (0.43 mg, 500 nmol, dissolved in 41.7 µL of acetonitrile) was added to the solution, which was gently mixed. Reaction control was performed via LC-ESI mass spectrometry. After 1 hour at room temperature the crude product was purified by semi-preparative reversed-phase chromatography using 0.1 M triethylammonium acetate (pH 7.0)/acetonitrile gradient as eluent. Fractions containing 13 (triethylammonium salt) were pooled and the solvent was evaporated. The residue was coevaporated three times with water and dissolved in 1.0 mL of water. Finally, the product solution was transferred into its sodium salt by cation-exchange chromatography. Fractions containing 13 (sodium salt) were pooled (detected by its blue color), the solvent was evaporated and the residue was dissolved in 220 µL of water (PCR grade). The yield of the triphosphate was determined by UV spectroscopy at 662 nm using the extinction coefficient of MR121: $\epsilon=105000$ M$^{-1}$ cm$^{-1}$ (N. Marmé et al., Chem. Phys. Lett. 2005, 408, 221-225).

Yield: 70.9 nmol (323 nmol/mL) of 13 (28%).

ESI-MS (m/z): [M-2H]$^-$ calcd for $C_{48}H_{70}N_8O_{24}P_3S_2^+$ (protonated form, cation), 1298.18. found 1296.82.

Example 3

Primer Extension Experiments 1.0 nmol DNA primer of the sequence 5'-T TTC CTC CTG CAC CGT-3'(SEQ. ID NO: 1) and 1.2 nmol DNA template of the sequence 3'-TTT GGA AAG GAG GAC GTG GCA AAA AA-5' (SEQ. ID NO: 2) both prepared by standard solid-phase phosphoramidite based oligonucleotide synthesis were dissolved in water in order to obtain a final reaction volume of 30 µL. Then 1 µL of 100 mM MnCl$_2$ and 3 µL of 10× ThermoPol Buffer (100 mM KCl, 100 mM (NH$_4$)$_2$SO$_4$, 200 mM Tris-HCl, 20 mM MgSO$_4$, 1% Triton X-100, pH 8.8 at 25° C., New England Biolabs) were added. The solution was heated to 95° C. for 5 minutes and then allowed to cool to room temperature within 30 minutes. Afterwards 1.0 to 2.5 nmol (1.0 to 2.5 µL, 1 nmol/µL) of 3 or 1 nmol (3.1 µL, 0.323 nmol/µL) of 13 were added. Furthermore, 0.125 U of PPiase Pyrophosphatase (0.104 µL, 1.2 U/µL), Roche Applied Science) were added unless otherwise indicated below. Finally, 2 U of Therminator™ II DNA Polymerase (1 µL, 2 U/µL) in storage buffer (100 mM KCl, 10 mM Tris-HCl, 0.1 mM EDTA, 1 mM DTT, 50% glycerol (v/v), pH 7.4 at 25° C., New England Biolabs) were added.

Final concentrations: 33 µM primer strand, 40 µM template strand, 33.3 to 83.3 µM triphosphate, 4.0 mM MnCl$_2$, 2.0 mM MgCl$_2$, 1.0 mM KCl, 1.0 mM (NH$_4$)$_2$SO$_4$, 2.0 mM Tris-HCl, 0.2 mM MgSO$_4$, 0.01% Triton X-100, 0.06 U/µL Therminator II DNA Polymerase, 4.17 mU/µL PPiase Pyrophosphatase.

The solution was gently mixed at 62° C. for 10 or 30 minutes and then the reaction was quenched with 3.0 µl of EDTA (50 mM). The reaction mixtures were analyzed at a concentration of 1 µM by LC-ESI mass spectrometry in the negative-ion mode.

Results:

| dNTP | 3 | 3 | 3 | 3 | 13 |
|---|---|---|---|---|---|
| c(dNTP) [µM] | 33.3 | 83.3 | 33.3 | 83.3 | 33.3 |
| PPiase | yes | yes | no | no | Yes |
| time [min] | 30 | 30 | 30 | 30 | 10 |
| template | | | | | |
| MW$_{calcd}$ [DA]/ MW$_{found}$ [DA] primer | 8141.4/ 8145.8 | 8141.4/ 8144.4 | 8141.4/ 8145.1 | 8141.4/ 8144.1 | 8141.4/ 8142.4 |
| MW$_{calcd}$ [DA]/ MW$_{found}$ [DA] primer + dNTP | 4759.2/ 4759.3 | 4759.2/ not detected | 4759.2/ 4759.6 | 4759.2/ not detected | 4759.2/ 4758.4 |
| MW$_{calcd}$ [DA]/ MW$_{found}$ [DA] primer − dT | 5108.4/ 5108.2 | 5108.4/ 5108.1 | 5108.4/ 5108.3 | 5108.4/ 5108.4 | 5882.4/ 5881.8 |
| MW$_{calcd}$ [DA]/ MW$_{found}$ [DA] primer − dT + dNTP | 4455.0/ not detected | 4455.0/ not detected | 4455.0/ 4455.9 | 4455.0/ not detected | 4455.0/ not detected |
| MW$_{calcd}$ [DA]/ MW$_{found}$ [DA] primer + dNTP − NO$_2$ | 4804.1/ not detected | 4804.1/ not detected | 4804.1/ 4804.4 | 4804.1/ 4805.5 | 5578.1/ not detected |
| MW$_{calcd}$ [DA]/ MW$_{found}$ [DA] | 5063.4/ not detected | 5063.4/ not detected | 5063.4/ 5065.7 | 5063.4/ not detected | 5837.4/ not detected |

Conclusions:

Triphosphates 3 and 13 were accepted as substrates by Therminator II DNA polymerase and can be incorporated efficiently depending on the triphosphate concentration. Addition of pyrophosphatase led to a cleaner and faster reaction. A triphosphate concentration of 83.3 µM led to a complete incorporation of the modified triphosphate.

Example 4

Cleavage of the 3'-O-nitro group 10 to 100 nmol of 3'-O-nitro-thymidine 2 were dissolved in an aqueous solution of cysteamine-NaOH (pH 9.0) to obtain a final nucleoside concentration of 0.17 to 1.7 nmol/µL and a final cysteamine concentration of 1.0 to 2.0 M.

Reaction control was performed via analytical reversed-phase chromatography using 0.1 M triethylammonium acetate (pH 7.0)/acetonitrile gradient as eluent. Quantitative cleavage of the nitrate group was obtained after 5 minutes at 50° C. and was verified by co-injection with the unmodified thymidine 14.

The invention claimed is:

1. A method for analyzing a DNA sequence comprising the steps of
   a) providing a nucleic acid template with a primer hybridized to said template forming a primer/template hybridization complex,
   b) adding DNA polymerase, and at least one labeled deoxynucleoside tri- or tetraphosphate comprising a 3'-nitrate and a detectable label covalently bound to the oxygen atom of an oxymethyl or oxyallyl or oxypropargyl substitution of a nucleobase, and a pyrophosphatase,
   c) subjecting said reaction mixture to conditions which enable a DNA polymerase catalyzed primer extension reaction,
   d) determining, whether said compound has been incorporated into said primer/template hybridization complex,
   e) simultaneously removing the 3'-nitrate group and optionally said label from said complex by means of adding a sulfide or a mercaptane, and
   f) repeating steps b) to e) at least once.

2. The method according to claim 1, wherein a different labeled deoxynucleoside tri- or tetraphosphate compound is added during repeat of step b).

3. The method according to claim 1, wherein a mixture of 4 differently labeled deoxynucleoside tri- or tetraphosphate compounds representing A, G, C and T/U are used in step b).

* * * * *